United States Patent [19]

Kanegaonkar

[11] Patent Number: 5,035,236
[45] Date of Patent: Jul. 30, 1991

[54] FILTRATION DEVICE FOR RESPIRATORY GASSES WITH HEAT AND MOISTURE EXCHANGE

[75] Inventor: Rahul G. Kanegaonkar, Hythe, England

[73] Assignee: Smiths Industries Public Limited Company, London, England

[21] Appl. No.: 540,266

[22] Filed: Jun. 19, 1990

[30] Foreign Application Priority Data

Jul. 18, 1989 [GB] United Kingdom ............... 8916361

[51] Int. Cl.$^5$ ..................... A61M 16/10; B01D 27/07; B01D 29/07
[52] U.S. Cl. .......................... 128/201.13; 128/205.27; 128/205.29; 55/498; 55/DIG. 35; 210/493.1
[58] Field of Search ...................... 128/201.13, 205.27, 128/205.29; 55/498, 514, DIG. 35; 210/493.2, 493.1, 493.5

[56] References Cited

U.S. PATENT DOCUMENTS

| | | | |
|---|---|---|---|
| 2,593,293 | 4/1952 | Giauque | 210/493.2 |
| 2,720,279 | 10/1955 | James | 55/498 |
| 2,897,971 | 8/1959 | Gewiss | 210/493.5 |
| 3,076,555 | 2/1963 | Jackson et al. | 210/493.1 |
| 3,803,817 | 4/1974 | Lewis . | |
| 4,036,616 | 7/1977 | Byrns | 55/498 |
| 4,232,667 | 11/1980 | Chalon et al. | 128/203.26 |
| 4,239,625 | 12/1980 | Hlavinka | 210/321.3 |
| 4,516,573 | 5/1985 | Gedeon | 128/201.13 |
| 4,557,261 | 12/1985 | Rügheimer | 128/202.27 |
| 4,619,675 | 10/1986 | Watanabe . | |
| 4,798,676 | 1/1989 | Matkovich | 128/206.16 X |

FOREIGN PATENT DOCUMENTS

| | | | |
|---|---|---|---|
| 689201 | 6/1964 | Canada | 210/493.1 |
| 0205072 | 12/1986 | European Pat. Off. . | |
| 269589 | 6/1988 | European Pat. Off. | 128/205.29 |
| 1576495 | 5/1970 | Fed. Rep. of Germany | 55/498 |
| 155215 | 9/1983 | Japan | 55/498 |
| 2221844 | 7/1989 | United Kingdom | 128/205.29 |

Primary Examiner—Edgar S. Burr
Assistant Examiner—Eric P. Raciti
Attorney, Agent, or Firm—Pollock, Vande Sande and Priddy

[57] ABSTRACT

A heat and moisture exchanger for use in medico-surgical applications has an element formed by a strip of bacterial filter material that is folded laterally into pleats and bent into a loop so that the folds extend radially. The element is sealed around its outer edge into a circular casing having axial, tapered ports at its opposite ends. A conical gas diverter is sealed into a central opening of the element on each side. Exhaled gas warms and moistens the element; inhaled gas is filtered and takes up some of the heat and moisture from the element. The exchanger is symmetrical so that it can be used either way around.

9 Claims, 2 Drawing Sheets

FILTRATION DEVICE FOR RESPIRATORY GASSES WITH HEAT AND MOISTURE EXCHANGE

BACKGROUND OF THE INVENTION

This invention relates to heat and moisture exchange devices.

Heat and moisture exchange devices are used in medico-surgical applications to take up heat and moisture from a patient's exhaled breath passing through the device and to transfer it to inhaled gas. One disadvantage with the presently available exchange devices, is that they impede the flow of the gas, leading to a pressure drop across the exchange element. This pressure drop can be reduced by increasing the area of the element exposed to the gas. This, however, makes the element larger and heavier, thereby correspondingly increasing the size and weight of the housing which may cause discomfort to the patient. It can also increase the dead space within the casing and increases the cost of the device itself, its packaging, transport and storage. Some devices must be connected in a particular orientation in order to prevent the build up of condensation in the device. This is a disadvantage because it requires care to be taken by the user in connecting the device into the patient breathing circuit.

BRIEF SUMMARY OF THE INVENTION

It is an object of the present invention to provide a heat and moisture exchange device that can be used to alleviate the above-mentioned problems.

According to one aspect of the present invention there is provided a heat and moisture exchange device for transferring heat and moisture in exhaled respiratory gas to inhaled respiratory gas including an outer casing and an exchange element within the casing, the exchange element comprising a strip of material folded into a plurality of pleats laterally of the length of the strip, and the strip being bent into a loop such that the folds of the pleats extend radially of the loop in two parallel planes substantially normal to the direction of flow of respiratory gases through the element.

The opposite ends of the strip are preferably joined together. The loop may have a central opening that is blocked by a material impervious to the respiratory gas. The central opening may have a gas diverter mounted therein to divert gas onto the exchange element and may have two gas diverters, one mounted on each side of the element. The gas diverters may be of conical shape. The exchange element is preferably sealed around its outer edge in the casing by a settable sealing compound. The casing may be of circular section, the exchange element being located axially within the casing with the planes of the folds of the pleats extending transversely of the casing, and the casing having a first port arranged axially on one side of the element and a second port arranged axially on the other side of the element. The device is preferably of symmetrical configuration and may have a tapered port at each end which communicates with a respective side of the exchange element.

The exchange element is preferably made of a filter material, the exchange element being arranged in the casing such that gas flowing through the device is filtered. The filter material is preferably a bacterial filter material and may be of a glass fibre membrane treated with silicone oil.

According to another aspect of the present invention there is provide a method of making a heat and moisture exchange device comprising the steps of: folding a strip of material laterally at equal intervals in opposite senses to form pleats; compressing the pleats into a pack such that adjacent pleats contact one another, the pack having two opposite faces between which the folds of the pack extend; sealing together adjacent pleats on one face; pulling opposite end folds of the pack from adjacent the other face around the one face to form a loop with the folds of the pleats extending radially; joining the opposite end folds together; blocking any space at the center of the loop; inserting the loop into a casing; and sealing the outer edge formed by the other face of the pack with the inside of the casing such that exhaled warm, moist gas flowing through the device in one direction flows through the material and a part of the heat and moisture is retained by the material, whereas inhaled gas flows through the material in the opposite direction and is warmed and moistened by the retained heat and moisture.

The adjacent pleats on the one face are preferably sealed together by coating the one face with a flexible, settable sealing compound. The outer edge of the loop may be sealed in the casing by a settable sealing compound.

A heat and moisture exchange device for medical ventilation gases, and its method of manufacture, in accordance with the present invention, will now be described, by way of example, with reference to the accompanying drawings.

DETAILED DESCRIPTION OF THE PREFERRED EMBODIMENT

Figure 1:
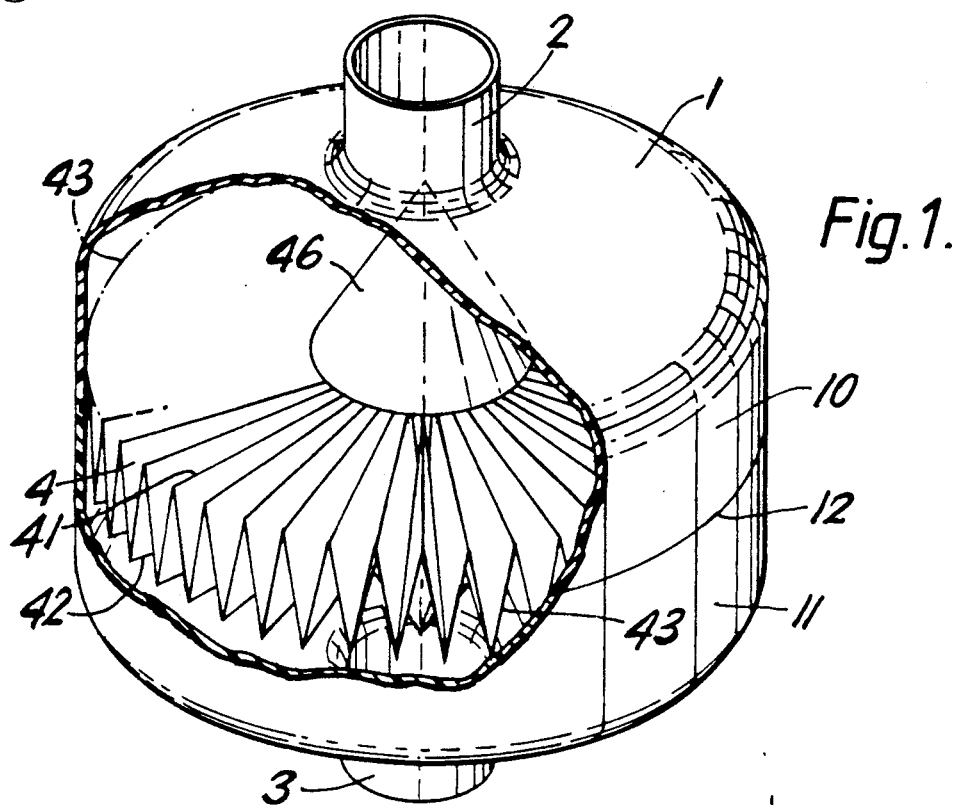
FIG. 1 is a perspective view of the exchange device.
Figure 2:
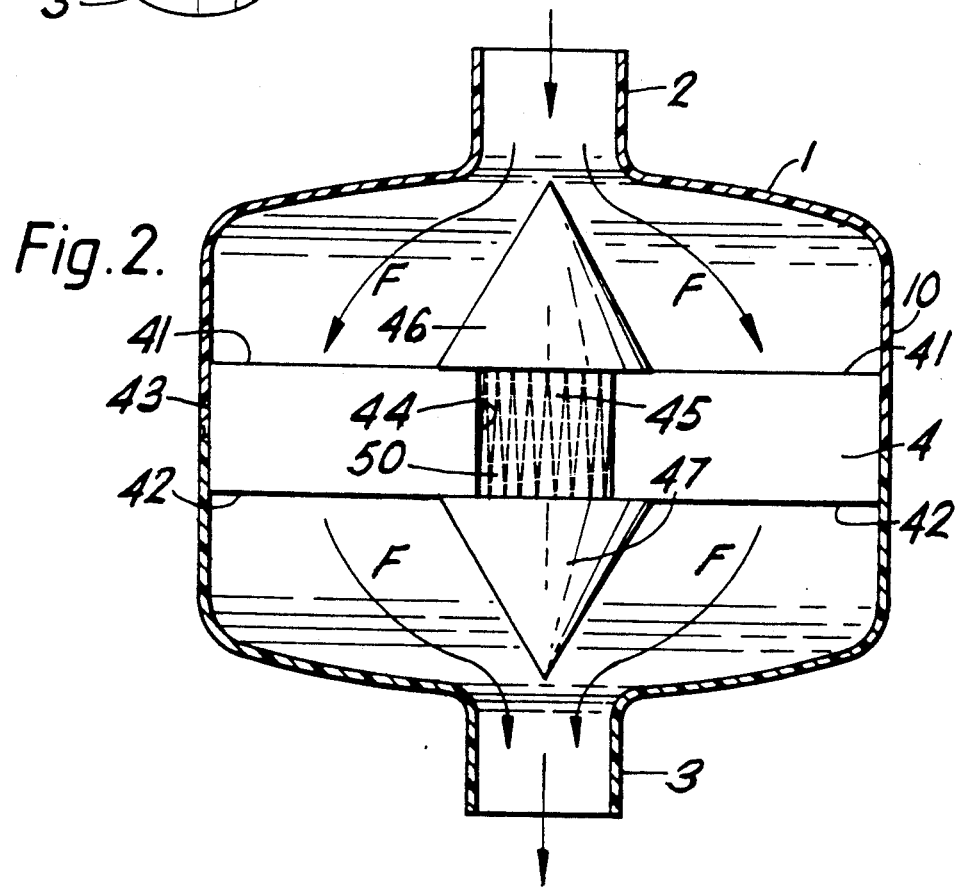
FIG. 2 is a sectional side elevation view of the exchange device.

The heat and moisture exchange device comprises a moulded plastics casing 1 with an inlet port 2 and an outlet port 3, the casing containing an exchange element 4.

The casing 1 is moulded in two parts 10 and 11, from a hard plastics material such as nylon or PVC, which are joined together along a circumferential split line 12. The casing 1 is of cylindrical shape and circular section with the inlet 2 and outlet 3 located axially in line and communicating with opposite sides of the element 4. The inlet 2 and outlet 3 are conventional luer taper or anaesthetic taper fittings and may be male, female or of a universal form incorporating a coaxial arrangement of a male and female coupling.

The exchange element 4 is made of a high efficiency, bacterial filtration medium such as a glass fibre membrane treated with a silicone oil, such as Syloff AVA sold by the Whatman Paper Company.

The exchange element 4 takes up heat and moisture in exhaled breath passing through the element 4 and transfers it to gas passing through the element in the opposite direction. The element 4 is permeable to gases but impermeable to bacteria and viral particles either by sieving these bacteria and particles from the gas stream or by providing a tortuous path through the element which causes these and other particles to be impeded upon the surface of the element because their greater momentum prevents them from circumnavigating the fibres of the element. In this respect, the element also acts as a filter as well as a heat and moisture exchange element.

The element 4 is in the form of a pleated circular loop of filter material with the folds 41 and 42 of the pleats extending radially. The folds 41 lie in a plane transverse to the direction of flow through the device as indicated by the arrows F; the opposite folds 42 lie in a plane parallel to that including the folds 41 but located closer to the outlet 3 of the device. The outer edge 43 of the exchange element 4 is sealed to the inner surface of the casing 1 such that there is no path for gas flow between the exchange element and the casing. In this respect, an adhesive or settable sealing compound can be used.

The inner edge 44 of the exchange element 4 is sealed, with an adhesive or settable sealing compound, to a gas-impermeable core piece 45 which extends through the center of the element and blocks passage of gas through the center. The core piece 45 is a hollow moulding of a light plastics material which is cylindrical in shape and provided with two flow diverters 46 and 47 at opposite ends. Both diverters 46 and 47 are of conical shape with a base that overlaps the inner edge 44 of the upper and lower surface of the exchange element 4. The exchange device is, therefore, of symmetrical configuration. Instead of using a gas-impermeable core piece, this could be replaced with an element having filtering and heat and moisture exchange properties similar to those of the glass fibre membrane.

In use, the inlet 2 is connected to a ventilation circuit which may include ventilation or anaesthetic equipment or may simply be open to atmosphere. The lower outlet 3 is connected via tubing to a tracheal tube or breathing mask. When the patient inhales, gas enters the device in a downwardly direction (although the device can be used in any orientation) through the inlet 2 and is diverted radially outwardly by the upper diverter 46 onto the upper surface of the element 4. Pressure difference across the element 4 causes gas to flow through the inclined faces of the element between the folds 41 and 42 of the pleats. Gas passing through the exchange element 4 flows out of the device through the outlet 3. When the patient exhales, gas flows through the device in the opposite direction, from the outlet to the inlet.

By mounting a diverter 46 and 47 on both sides of the filter element 4 it enables the device to be used either way around, providing that the inlet and outlet couplings 2 and 3 are compatible with the connections to the device. This is an advantage because it means that no special care need be taken to ensure that the device is correctly oriented.

Figure 3:
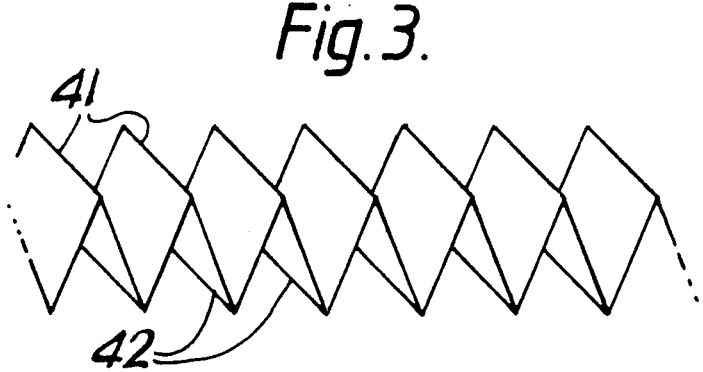
FIGS. 3 to 6 illustrate steps in the manufacture of a part of the exchange element.
Figure 4:
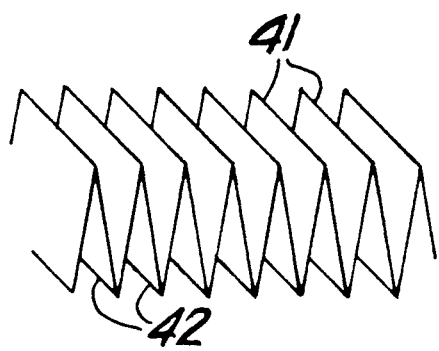
Figure 5:
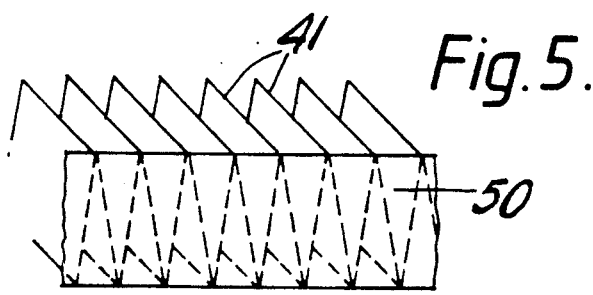
Figure 6:
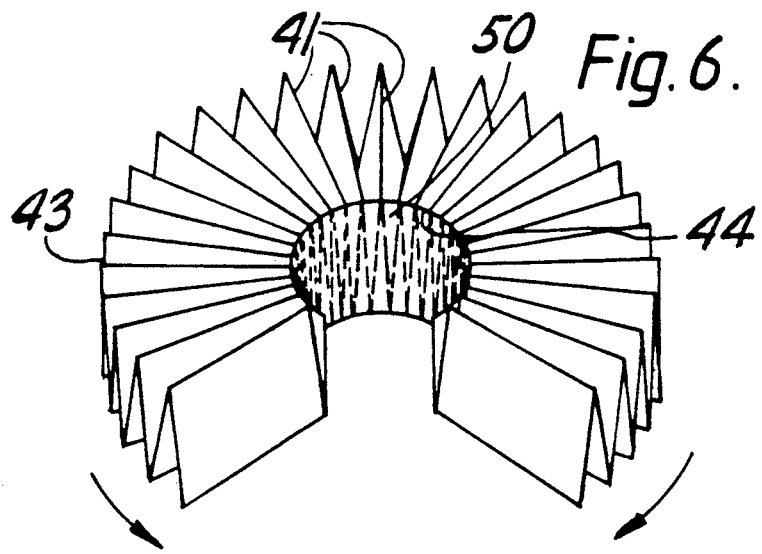

The exchange element 4 is preferably made in the manner shown in FIGS. 3 to 6. First, as shown in FIG. 3, a strip of the filter material, which is typically 21 mm wide and 2857 mm long, is folded laterally at equal intervals in opposite senses to form fifty-one pleats each of length 56 mm. The strip is then compressed into a pack so that adjacent pleats come into contact with one another in the manner shown in FIG. 4. Next, the pleats on one face of the pack, which will eventually form the inner edge 44 of the exchange element 4, are sealed by coating the face with a flexible, settable sealing compound 50, as shown in FIG. 5. The opposite end folds of the pack are then gripped close to the opposite face and pulled around, as shown in FIG. 6, to form a loop. An adhesive is used to seal these end folds together. The element now formed resembles a ruff with the folds 41 and 42 of the pleats extending radially and with an outer diameter of 56 mm, an inner diameter of 14 mm and a thickness of 27 mm. Prior to installation in the casing 1, the outer edge 43 of the element is sealed and coated with a similar compound to that applied to the inner edge 44. The element 4 is preferably installed in the casing 1 before the sealing compound is set, so that it conforms to the inner surface of the casing 1 and seals with it. The core piece 45 with the flow diverters 46 and 47 are mounted on the exchange element 4 before installation in the casing.

Because the folds 41 and 42 of the exchange element 4 extend radially, the average separation between the pleats is greater than in previous exchange elements employing axially arranged pleats. This gives the device a more open construction thereby admitting more gas to the element which in turn allows more gas to pass through the entire element and reduces the resistance to flow provided by the element. In this way, the size of element can be smaller than that of a conventional exchange element having the same resistance to flow. The exchange device of the present invention can, therefore, be made smaller and lighter than previous devices or with reduced resistance to flow.

What I claim is:

1. A medico-surgical heat and moisture exchange device including means for transferring heat and moisture in exhaled respiratory gas to inhaled respiratory gas comprising an outer casing having an inlet port adapted for connection to a ventilation circuit and an outlet port adapted for connection to a patient's respiratory system, said means further comprising an exchange element within the casing intermediate said inlet and outlet ports so positioned that gas flow through said casing between said inlet and outlet ports passes through said exchange element, said exchange element comprising a strip of material folded into a plurality of pleats laterally of the length of the strip, and said strip being bent into a loop such that the folds of the pleats extend radially of the loop in two parallel planes substantially normal to the direction of flow of respiratory gases through the said exchange element such that, on exhalation, gas flows from the outlet port to the inlet port through the pleated exchange element giving up at least a part of its heat and moisture to the pleated exchange element and such that, on inhalation, gas flows in the opposite direction from the inlet to the outlet through the pleated exchange element taking up at least a part of the heat and moisture in the exchange element so that the inhaled gas is thereby warmed and moistened.

2. A medico-surgical device according to claim 1, wherein said strip has opposite ends which are joined together.

3. A medico-surgical device according to claim 1 or 2, wherein said loop has a central opening and a gas diverter which is mounted within said central opening to divert gas onto the exchange element.

4. A medico-surgical device according to claim 1 or 2, wherein said exchange element has an outer edge, said exchange element being sealed around said outer edge in the casing by a settable sealing compound.

5. A medico-surgical device according to claim 1, wherein said outer casing is of circular section, said exchange element being located axially within the casing with the planes of the folds of the pleats extending transversely of the casing, said inlet port being arranged axially at one end of the casing and said outlet port being arranged axially at an opposite end of the casing.

6. A medico-surgical device according to claim 1, 2 or 5, wherein the exchange element is of a filter material and the exchange element is located in the casing such that gas flowing through the device is filtered.

7. A medico-surgical device according to claim 6, wherein the filter material is a bacterial filter material.

8. A combined heat and moisture exchange device and filter for use in medico-surgical applications including means for filtering and transferring heat and moisture in exhaled respiratory gas to inhaled respiratory gas comprising: an outer casing of circular section having an outlet port for connection to a patient and an inlet port open to a supply of respiratory gas; an exchange element sealed around an outer edge within the casing between said inlet and outlet ports, said exchange element comprising a strip of filter material folded into a plurality of pleats laterally of the length of the strip and bent into a circular loop with opposite ends of the loop joined together and with the folds extending radially of the loop in two parallel planes substantially normal to an axis of the casing between said ports, said loop having a central opening within which is mounted a gas diverter such that all gas flowing between said ports flows through the material of said exchange element and such that, on exhalation, gas flows from said outlet port to said inlet port through the pleated exchange element and such that, on inhalation, gas flows in the opposite direction from said inlet port to said outlet port through the pleated exchange element taking up at least a part of the heat and moisture in the exchange element so that the inhaled gas is thereby warmed and moistened.

9. A method of making a medico-surgical respiratory heat and moisture exchange device by folding a strip of material laterally at equal intervals in opposite senses to form pleats; compressing the pleats into a pack such that adjacent pleats contact one another, the pack having two opposite faces between which the folds of the pack extend; sealing together adjacent pleats on one face; pulling opposite end folds of the pack from adjacent the other face around the one face to form a loop with the folds of the pleats extending radially; joining the opposite end folds together; filling any space at the center of the loop; inserting the loop into a casing and sealing the outer edge formed by the other face of the pack with the inside of the casing such that exhaled warm, moist gas flowing through the device in one direction flows through the material and a part of the heat and moisture is retained by the material, whereas inhaled gas flows through the material in the opposite direction and is warmed and moistened by the retained heat and moisture.

* * * * *